United States Patent [19]
Koenig

[11] Patent Number: 4,918,072
[45] Date of Patent: Apr. 17, 1990

[54] PLATELET AGGREGATION INHIBITING COMPOSITION

[75] Inventor: Horst Koenig, Ludwigshafen, Fed. Rep. of Germany

[73] Assignee: BASF Aktiengesellschaft, Ludwigshafen, Fed. Rep. of Germany

[21] Appl. No.: 18,800

[22] Filed: Feb. 20, 1987

Related U.S. Application Data

[63] Continuation-in-part of Ser. No. 917,045, Oct. 9, 1986, abandoned.

[30] Foreign Application Priority Data

Oct. 9, 1985 [DE] Fed. Rep. of Germany ....... 3535949

[51] Int. Cl.$^4$ .............................................. A61K 31/50
[52] U.S. Cl. ..................................................... 514/247
[58] Field of Search ......................................... 514/247

[56] References Cited

U.S. PATENT DOCUMENTS 3,261,859  7/1966  Dengel ................................. 260/465
4,258,185  3/1981  Nakao et al. ......................... 544/114
4,438,131  3/1984  Ehrmann et al. ................. 260/465 E
4,474,785 10/1984  Rossy et al. ......................... 544/235

FOREIGN PATENT DOCUMENTS 1154810  4/1961  Fed. Rep. of Germany .
3124699  6/1981  Fed. Rep. of Germany .

OTHER PUBLICATIONS

Rossy et al., Chem. Abst. 101(25):230558w (1984).
Liste Pharmindex III/84, pp. 648; 1024–1025.

Primary Examiner—Douglas W. Robinson
Attorney, Agent, or Firm—Keil & Weinkauf

[57] ABSTRACT

A combination of a phenylacetonitrile and a pyridazinone derivative can be used for the treatment of thromboembolic disorders.

3 Claims, No Drawings

PLATELET AGGREGATION INHIBITING COMPOSITION

This is a continuation-in-part of Ser. No. 917,045, filed Oct. 9, 1986, now abandoned.

The present invention relates to a novel combination product for the treatment of thromboembolic disturbances of blood flow.

It is known that phenylacetonitriles with basic substituents (cf. German Patent No. 1,154,810 and European Laid-Open Application No. 64,158) can be used for the treatment of cardiac disorders caused by insufficient tissue perfusion (ischemia) (cf. Liste Pharmindex III/84, Isoptin ® and Procorum ®). They have both a vasodilatory action and a cardioprotective and platelet aggregation-inhibiting action. It is also known (cf. German Laid-Open Applications DOS Nos. 2,845,220 and DOS 3,124,699 and European Laid-Open Application No. 117,403) that certain pyridazinone derivatives have a platelet aggregation-inhibiting action.

We have found that the activity of the phenylacetonitriles can be greatly increased by means of pyridazinone derivatives.

The present invention relates to a drug which contains a compound of the formula I

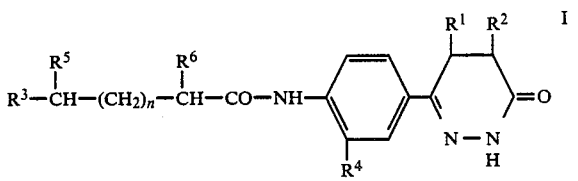

where $R^1$, $R^2$, $R^3$, $R^4$, $R^5$ and $R^6$ are identical or different and are each hydrogen, halogen, $C_1$–$C_4$-alkyl or $C_1$–$C_4$-alkoxy and $R^7$ is a saturated or unsaturated hydrocarbon radical of not more than 20 carbon atoms, and a pyridazinone derivative of the formula II

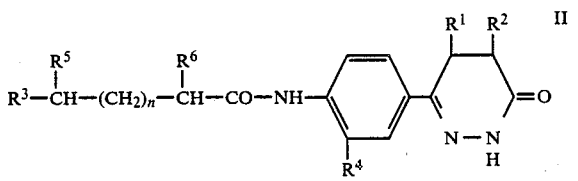

where $R^1$ is hydrogen or methyl, $R^2$ is hydrogen or, together with $R^1$, forms methylene or ethylene, $R^3$ is (a) a group of the formula

where the dashed line may be an additional bond and, where relevant, $R^7$ is hydrogen or $C_1$–$C_4$-acyl, or (b) a group of the formula

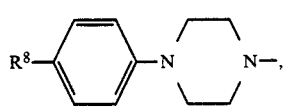

where $R^8$ is hydrogen or $C_1$–$C_4$-acyl, or (c) 1,3-tetrahydroisoquinolin-2-yl, $R^4$ is hydrogen or, together with $R^3$, forms a direct bond or methylene, $R^5$ is hydrogen or methyl, $R^6$ is hydrogen or halogen and n is 0 or 1, compound I being present in an amount of 50–450 parts by weight and compound II in an amount of 3–50 parts by weight.

The compounds of the formula I can be present in the drug in free form or in the form of their physiologically tolerated salts. Hydrochloric acid, sulfuric acid, phosphoric acid, acetic acid, malonic acid, succinic acid, fumaric acid, maleic acid, citric acid, tartaric acid, lactic acid, amidosulfonic acid and oxalic acid are suitable for salt formation with the compounds I. The compounds of the formula I are preferably used in the form of their hydrochlorides.

The stated mixing ratio is based on the free form of the compounds I, the preferred mixing ratio being about 100 parts of compound I and 10 parts of compound II.

The superior action of the novel combination can be demonstrated by determining the platelet aggregation in the following experiments:

1. Platelet-rich plasma is obtained from venous citrated blood by centrifuging (300 g, 10 min duration at 4° C). Photometric measurement of platelet aggregation is carried out with the addition of $MgCl_2$ (final concentration 10 mmol/l) and of collagen Stago (final concentration 0.02 mg/ml), in an Mk 3 Born aggregometer. The maximum change in extinction per second is used as a measure of aggregation.

The aggregation-inhibiting activity of the substances is measured after an incubation time of 10 minutes.

The concentration which causes 50% inhibition of aggregation is determined as the EC 50%. 2. The substances and the combination are administered orally to beagles weighing from 10 to 15 kg. Before, as well as 2 and 4 hours after, administration of the substance, venous blood was taken and rendered incoagulable by adding citrate, after which platelet-rich plasma was obtained from this blood by centrifuging (300 g, minutes duration at 4° C.). The addition of adrenalin (final concentration $5 \times 10^{-8}$ mol/l) and collagen (final concentration $2 \times 10^{-3}$ g/l) to the platelet-rich plasma induced aggregation, which was measured as extinction in a Mk 3 Born aggregometer. The maximum change in extinction per second is used as a measure of aggregation. The percentage inhibition of aggregation was determined by comparing the values before and after administration of the substance.

The following results were obtained in the experiments:

| Experiment | Substance | Dose (mg/kg) | Aggregation inhibition (%) |
|---|---|---|---|
| 2 | Amipizone* | 0.1 | 2.0 |
| 2 | Verapamil | 0.1 | 2.8 |
| 2 | Amipizone + Verapamil | 0.1 + 0.1 | 18 |
| 1 | Amipizone | 0.005 | 23 |
| 1 | Amipizone | 0.1 | 48 |
| 1 | Verapamil | 21.5 | 17 |
| 1 | Amipizone + Verapamil | 0.005 + 21.5 | 50 |
| 1 | Amipizone | 0.1 | |

| Experiment | Substance | Dose (mg/kg) | Aggregation inhibition (%) |
|---|---|---|---|
| | Verapamil | 21.5 | 77 |

*Amipizone: cf. European Laid-Open Application 117,403, Example 13.

The novel combination is useful for the treatment and prophylaxis of disorders caused by platelet aggregation. These include thromboembolic disorders of the heart, brain, and the peripheral, arterial vascular system. Examples of such disorders are cardiac infarction, strokes and obliterative arteriosclerosis.

The novel combination is also useful for the treatment and prophylaxis of diseases caused by the release of vasoactive substances from aggregating platelets, for example migraines, vasospastic angina and Raynaud's disease. It is furthermore useful for the prevention of complications during surgical measures, such as vascular prostheses and shunts.

When the novel combination is used, fewer side effects are observed than would be expected after administration of the individual components.

The combination according to the invention can be administered orally in a conventional manner.

The dosage depends on the age, condition and weight of the patient and on the route of administration. As a rule, the daily dose is from about 50 to 500 mg, preferably from 50 to 200 mg, with compound I and from about 3 to 50 mg, preferably about 10 mg, of compound II per patient.

The novel combination may be employed in the conventional solid or liquid pharmaceutical forms, such as tablets, film-coated tablets, capsules, powders, granules, coated tablets, pellets, controlled release pellets or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retardants and/or antioxidants (cf. H. Sucker et al., Pharmazeutische Technologie, Thieme-Verlag, Stuttgart, 1978). The administration forms thus obtained normally contain from 10 to 99% by weight of the active compound.

EXAMPLE 1

Tablets having the following composition were press in a conventional manner on a tablet press:

400 mg of verapamil hydrochloride
10 mg of 2-(1,2,3,4-tetrahydroquinolin-2-on-6-yl)-3,4-diazabicyclo[4.1.0]hept-2-en-5-one
72 mg of corn starch
13 mg of gelatin
35 mg of lactose
25 mg of carboxymethylcellulose
17.5 mg of talc
3.5 mg of magnesium stearate

EXAMPLE 2

Tablet cores having the following composition were prepared in a conventional manner:

50 mg of Gallopamil
5 mg of 2-(2,3,4,5-tetrahydrobenzo[b]azepin-2-(1H)-on-7-yl)-3,4-diazabicyclo[4.2.0]oct-2-en-5-one
50 mg of core material The core material consisted of 9 parts of corn starch, 3 parts of lactose and 1 part of Luviskol VA 64 (60:40 vinylpyrrolidone/vinyl acetate copolymer, cf. Pharm. Ind. 1962, 586). The sugar-coating material consisted of 5 parts of sucrose, 2 parts of corn starch, 2 parts of calcium carbonate and 1 part of talc.

The cores obtained were then coated with the above sugar-coating material.

EXAMPLE 3

To produce film-coated tablets, the tablet cores prepared as described in Example 2 were coated with a film coating having the following composition:

| Tylose | 0.7% | Corn starch | 2.0% |
|---|---|---|---|
| Kollidon 25 (PVP) | 0.4% | Calcium carbonate | 3.5% |
| Sucrose | 70.0% | Gum arabic | 2.5% |
| Finely divided silica | 1.4% | Titanium dioxide + | |
| Talc | 11.0% | Colorants | 8.5% |

EXAMPLE 4

Controlled release pellets suitable for introducing into hard gelatin capsules were prepared, each component being pelletized separately and the controlled release pellets then being introduced into the capsules either as a mixture or in succession.

Composition of the pellets per dose:

Controlled release pellets, compound I:
100 mg of Gallopamil hydrochloride
60 mg of cellulose powder
5 mg of corn starch
10 mg of talc
35 mg of ethylcellulose Controlled release pellets, compound II:
20 mg of 6-[p-3-(4-phenyl-1-piperidyl)-propionylaminophenyl]-4,5-dihydro-5-methyl-3(2H)-pyridazinone
20 mg of cellulose powder
10 mg of corn starch
10 mg of ethylcellulose

EXAMPLE 5

Pellets suitable for introducing into hard gelatin capsules were prepared, the pellets having the following composition:

300 mg of verapamil
5 mg of 6-[p-3-(4-phenyl-1-piperazinyl)-propionylaminophenyl]-4,5-dihydro-5-methyl-3(2H)-pyridazinone
80 mg of cellulose powder
30 mg of corn starch
5 mg of (R)Kollidon 30 (PVP)
20 mg of (R)Eudragit S (polymer of methylacrylic acid and methacrylate)
15 mg of talc.

I claim:

1. A pharmaceutical composition which comprises: a pharmaceutical carrier and a combination of a compound of the formula I

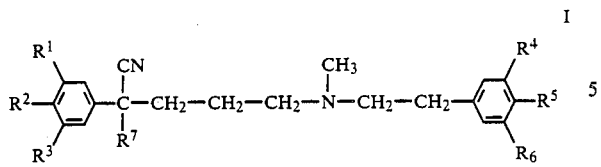

where $R^1$, $R^2$, $R^3$, $R^4$, $R^5$ and $R^6$ are identical or different and are each hydrogen or $C_1$-$C_4$-alkoxy, and $R^7$ is a $C_1$-$C_4$ alkyl, and a pyridazinone derivative of the formula II

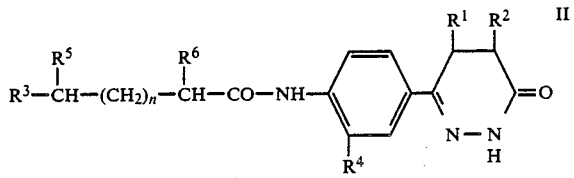

where $R^1$ is hydrogen or methyl, $R^2$ is hydrogen or, together with $R^1$ forms a methylene of ethylene, $R^3$ is a group of the formula

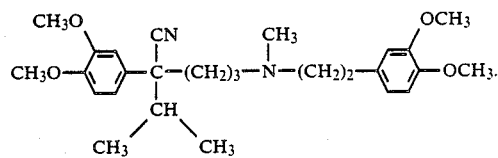

where $R^7$ is hydrogen or $C_1$-$C_4$-acyl $R^4$ is hydrogen or, together with $R^3$, forms a direct bond or methylend, $R^5$ is hydrogen or methyl, $R^6$ is hydrogen or halogen and n is 0 or 1, compound I being present in an amount 50-450 parts by weight and compound II in an amount of 3-50 parts by weight.

2. A composition as defined in claim 1, wherein compound I has the formula

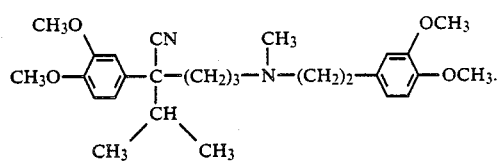

3. A composition as defined in claim 1, wherein compound I has the formula

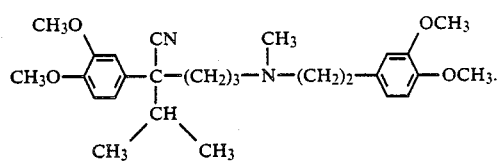

and compound II has the formula

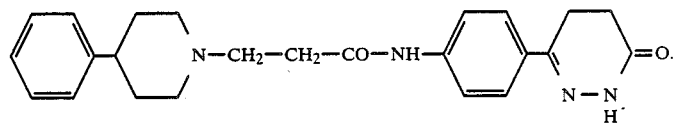

* * * * *

UNITED STATES PATENT AND TRADEMARK OFFICE
CERTIFICATE OF CORRECTION

PATENT NO. : 4,918,072

DATED : April 17, 1990

INVENTOR(S) : Horst KOENIG

It is certified that error appears in the above-identified patent and that said Letters Patent is hereby corrected as shown below:

Claim 1, column 5, line 23

"forms a methylene of ethylene" should read -- forms methylene or ethylene --

Claim 1, column 6, line 8

"methylend" should read -- methylene --

Signed and Sealed this

Ninth Day of July, 1991

Attest:

HARRY F. MANBECK, JR.

*Attesting Officer*  *Commissioner of Patents and Trademarks*